United States Patent [19]

Valia

[11] Patent Number: 5,196,416
[45] Date of Patent: Mar. 23, 1993

[54] TRANSDERMAL FLUX-ENHANCING PHARMACEUTICAL COMPOSITIONS COMPRISING AZONE, ETHANOL AND WATER

[75] Inventor: Kirti H. Valia, Indianapolis, Ind.

[73] Assignee: Eli Lilly and Company, Indianapolis, Ind.

[21] Appl. No.: 679,164

[22] Filed: Mar. 26, 1991

Related U.S. Application Data

[63] Continuation of Ser. No. 449,200, Dec. 12, 1989, abandoned, which is a continuation-in-part of Ser. No. 90,726, Aug. 28, 1987, abandoned.

[51] Int. Cl.$^5$ ............... A61K 31/55; A61K 31/50; A61K 31/505; A61K 31/44
[52] U.S. Cl. ................... 514/212; 514/253; 514/267; 514/352; 514/357; 514/428; 514/947
[58] Field of Search ............ 514/212, 947, 253, 267, 514/352, 357, 428

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,299,826 | 11/1981 | Luedders | 424/181 |
| 4,316,893 | 2/1982 | Rajadhyashka | 514/24 |
| 4,335,115 | 6/1982 | Thompson et al. | 424/181 |
| 4,405,616 | 9/1983 | Rajadhyaksha | 424/244 |
| 4,415,563 | 12/1983 | Rajadhyashka | 514/24 |
| 4,424,210 | 1/1984 | Rajadhyashka | 514/24 |
| 4,501,890 | 2/1985 | Nichols et al. | 514/267 |
| 4,552,872 | 11/1985 | Cooper et al. | 514/175 |
| 4,557,934 | 12/1985 | Cooper | 514/159 |
| 4,560,553 | 12/1985 | Zupan | 424/78 |
| 4,568,343 | 2/1986 | Leeper et al. | 604/896 |
| 4,594,243 | 6/1986 | Satoh et al. | 424/78 |
| 4,959,365 | 9/1990 | Francoeur et al. | 514/237.5 |

FOREIGN PATENT DOCUMENTS

| | | |
|---|---|---|
| 0129284 | 12/1984 | European Pat. Off. |
| 0161918 | 11/1985 | European Pat. Off. |
| 0245126 | 11/1987 | European Pat. Off. |
| 0271983 | 6/1988 | European Pat. Off. |
| 61-33128 | 2/1986 | Japan |
| 62-240628 | 10/1987 | Japan |
| 2014134 | 8/1979 | United Kingdom |

OTHER PUBLICATIONS

Chemical Abstracts No. 98:100968p (1982).
Touitou, International Journal of Pharmaceutics, 33, 37-43 (1986).

Primary Examiner—Richard L. Raymond
Assistant Examiner—Gary E. Hollinden
Attorney, Agent, or Firm—Nancy J. Harrison; Leroy Whitaker

[57] ABSTRACT

Permeation enhancement compositions are disclosed. Said compositions include from 30 to 70 parts by weight ethanol, from 0.1 to 10 parts by weight azone, from 30 to 80 parts by weight water and optionally from 10 to 30 parts by weight propylene glycol, which compositions provide increased percutaneous absorption of a pharmacologically active agent disposed therewith.

8 Claims, No Drawings

TRANSDERMAL FLUX-ENHANCING PHARMACEUTICAL COMPOSITIONS COMPRISING AZONE, ETHANOL AND WATER

CROSS-REFERENCE

This application is a file wrapper continuation of application Ser. No. 07/449,200, filed on Dec. 12, 1989, now abandoned which is a continuation-in-part of application Ser. No. 07/090,726, filed Aug. 28, 1987, now abandoned.

BACKGROUND OF THE INVENTION

Percutaneous or transdermal delivery of pharmacologically active agents has become feasible in recent years largely due to vehicles therefor which allow increased permeation of said agents into the body surface to which applied. Certain advantages are attendant to percutaneous drug delivery such as avoidance of the varied absorption and metabolism which can be encountered by oral therapy, avoidance of first pass hepatic metabolism, improved patient compliance as a result of a simplified therapeutic regimen and the like. In many cases, drugs which would appear to be ideal candidates for percutaneous delivery are found to have such low permeability that they cannot be delivered at therapeutically effective rates. In attempts to obviate this problem, various materials and compositions have been suggested as permeation enhancers to effect the transdermal delivery of the pharmacologically active agent. Among these are the following: dimethyl sulfoxide (U.S. Pat. No. 3,551,554); various 1-substituted azacycloalkan-2-ones including 1-dodecylazacycloheptan-2-one referred to hereinafter as azone (U.S. Pat. Nos. 4,562,075, 4,405,616, 4,326,893 and 3,989,816); sugar esters in combination with sulfoxide or phosphine oxide (U.S. Pat. Nos. 4,130,667, 4,130,643, 4,046,886, 3,952,099 and 3,896,238); lower alkyl amides (U.S. Pat. No. 3,472,931); certain aliphatic sulfoxides (U.S. Pat. No. 3,903,256); a composition containing glycerol monooleate, ethanol and isopropyl myristate (U.S. Pat. No. 4,335,115); a binary mixture of 1-dodecylazacycloheptan-2-one and a compound selected from a diol or a second N-substituted azacycloalkyl-2-one (U.S. Pat. No. 4,557,934); and polyethylene glycol monolaurate (U.S. Pat. No. 4,568,343). None of these references disclose or suggest the permeation enhancement compositions claimed herein for increasing the percutaneous absorption of pharmacologically active agents.

SUMMARY OF THE INVENTION

The present invention is directed to a permeation enhancement composition for providing increased percutaneous absorption of a pharmacologically active agent. The composition comprises from 30 to 70 parts by weight ethanol, from 0.1 to 10 parts by weight azone, from 30 to 69.9 parts by weight water, and optionally, from 10 to 30 parts by weight propylene glycol. The invention also relates to an improved method for the percutaneous administration of a pharmacologically active agent which includes placing and maintaining on a body surface a source of said agent and a permeation enhancement composition therefor in agent and composition transmitting relationship on said body surface the improvement wherein said permeation enhancement composition comprises from 30 to 70 parts by weight ethanol, from 0.1 to 10 parts by weight azone, from 30 to 69.9 parts by weight water, and optionally, from 10 to 30 parts by weight propylene glycol.

DETAILED DESCRIPTION OF THE INVENTION

The permeation enhancement compositions of the present invention effect the increased percutaneous absorption of the pharmacologically active agents disposed therein to an extent greater than that observed if any one component of said compositions were used alone as the permeation enhancement means for said agent. Without being bound by theory, it would appear that each of the ethanol, water and, when present, propylene glycol act individually as solvents for the pharmacologically active agents, the permeation of each of which is enhanced by the action of azone. Additionally, the ethanol and propylene glycol exhibit some permeation enhancement characteristics which, when taken in the aggregate with their solvent effects, renders compositions with azone which show exquisite permeation enhancement capacity.

The permeation enhancement compositions of the present invention utilize, in addition to ethanol, water and propylene glycol (if present), the known permeation enhancer azone. As noted above, chemically azone is 1-dodecylazacycloheptan-2-one and is prepared as described in U.S. Pat. No. 4,316,893 which is incorporated herein by reference. The present permeation enhancement compositions contain from 30 to 70 parts by weight ethanol (preferably 200 proof), from 0.1 to 10 parts by weight azone, and from 30 to about 80 parts by weight water. Optionally, from 10 to 30 parts by weight of propylene glycol may be added to the formulation. A preferred composition which contains propylene glycol is a composition containing from 30 to 50 parts by weight ethanol, from 0.1 to 10 parts by weight azone, from 30 to 50 parts by weight water and from 10 to 30 parts by weight propylene glycol. A particularly preferred composition which contains propylene glycol is a composition having 37 parts by weight ethanol, 3 parts by weight azone, 40 parts by weight water and 20 parts by weight propylene glycol. A preferred composition which does not contain propylene glycol is one containing from 35 to 70 parts by weight ethanol, from 0.1 to 10 parts by weight azone and from 35 to 69.9 parts by weight water. A particularly preferred composition which does not contain propylene glycol is one containing 52 parts by weight ethanol, 3 parts by weight azone and 45 parts by weight water. Formulation of these compositions may be achieved by conventional methods, as by the simple mixing of all components thoroughly. The above-noted ranges set forth for each component of the permeation enhancement compositions of the present invention are critical for achieving the unexpected increase in percutaneous absorption of pharmacologically active agents as illustrated hereinafter. However, the skilled artisan will readily appreciate that compositions containing diols other than propylene glycol and alcohols other than ethanol (such as 2-propanol) may find utility in permeation enhancement compositions as a component of the formulation. To the extent that any such formulation exhibits the characteristics of the present compositions, such formulations are considered to fall within the scope and spirit of the present invention.

The permeation enhancement compositions of the present invention are utilized to increase the percutaneous absorption of a pharmacologically active agent disposed therewith. "Increased percutaneous absorption" refers to absorption of a pharmacologically active agent to an extent greater than if said agent were not disposed with a permeation enhancement composition of the present invention. As used herein, the term "pharmacologically active agent" is used in its broad sense as meaning any agent which is administered for the purpose of providing some beneficial or therapeutic effect either locally or systemically. In general, this includes agents in all of the major therapeutic classes including, but not limited to, anti-infectives such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, antiinflammatory agents, antimigraine preparations, antimotion sickness agents, antinauseants, antineoplastics, antiparkinsonism agents, antipruritics, antipsychotics, antipyretics, antispasmodics including gastrointestinal and urinary; dopamine agonists, anticholinergics, sympathomimetics, xanthine derivatives, various cardiovascular agents including calcium channel antagonists, beta-blockers, antiarrhythmics, positive inotropic agents, antihypertensives, diuretics, vasodilators including general, coronary, peripheral and cerebral; central nervous system stimulants, corticosteroids, cough and cold preparations, decongestants, diagnostics, hormones, hypnotics, immunosuppressives, muscle relaxants, parasympatholytics, parasympathomimetics, psychostimulants, sedatives, tranquilizers and the like. Preferred pharmacologically active agents are those having cardiovascular effects. Of those preferred pharmacologically active agents, those compounds described in Examples 1 through 4, infra, are particularly preferred.

It is contemplated that the permeation enhancement compositions of the present invention will find utility in both humans and animals, i.e., will have both medical and veterinary applications for providing increased percutaneous absorption of pharmacologically active agents. It must be pointed out that as used herein, the term "percutaneous" refers not only to the passage of such agents through skin (typically intact) but also to the passage of pharmacologically active agents through membranous tissue such as mucosal membranes. For these purposes, various pharmaceutical dosage forms are available for percutaneous administration and are well known in the art and include, for example, creams, lotions" gels, ointments, suppositories, sprays, aerosols and any of a wide variety of transdermal devices for use in the relatively continuous administration of pharmacologically active agents as described in any of the following: U.S. Pat. No. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299 and U.S. Pat. No. 4,292,303 each of which is incorporated herein by reference. Preferred pharmaceutical dosage forms are transdermal devices. A particularly preferred transdermal device is as disclosed in U.S. Pat. No. 3,710,795. Of course, as other such dosage forms are developed the permeation enhancement compositions of the present invention shall also find applicability. It will be readily evident to the skilled artisan that the dosage form utilized may also incorporate certain pharmaceutically-acceptable excipients which are conventional in the art. These include, for example, gelling agents, cream and ointment bases and the like.

One or more pharmacologically active agents are present in the pharmaceutical dosage form in an effective amount, i.e., an amount calculated to achieve and maintain blood levels which will bring about the desired beneficial or therapeutic effect over the period of time desired. These amounts will vary depending upon the relative potency of the pharmacologically active agent utilized, the amount of such agent required for the desired beneficial or therapeutic effect, the physiological half-life of the agent, the specific formulation of the permeation enhancement composition used, and the like. Suffice it to say that conventional dose titration techniques, which are well within the skill of the artisan, may be utilized to determine the amount of the pharmacologically active agent present in the ultimate pharmaceutical dosage form for any specific situation encountered.

The pharmacologically active agent is administered by known techniques such as by placing a source (i.e., a pharmaceutical dosage form) containing said agent and permeation enhancement composition therefor (including any excipients if needed) on a body surface and maintaining said source on said body surface in agent and composition transmitting relation thereto. Alternatively, the permeation enhancement compositions of the present invention may be used separately from the pharmaceutical dosage form containing the pharmacologically active agent. For example, the body surface to which the pharmacologically active agent is to be applied may be pretreated with a permeation enhancement composition of the present invention prior to application of the pharmaceutical dosage form containing said agent.

In order to further illustrate the present invention, various of the permeation enhancement compositions described herein were formulated with pharmacologically active agents. These formulations were then tested for their capacity to permeate human cadaver skin using the apparatus and method described by Valia et. al. in *Drug Development and Industrial Pharmacy*, 10(7), 951-981 (1984) which is incorporated herein by reference. Briefly, the apparatus used was a skin permeation cell consisting of two cylindrical half-cells in mirror image. Each of the half-cells was composed of a solution compartment which was enclosed inside of a water jacket compartment. Each of the half-cells was equipped with a closable sampling port and a depression in the solution compartment which serves as the platform for a star-head rotating magnet. The magnets stirred the solution in the half-cells at a constant rate of 600 revolutions per minute by an external synchronous driving unit. Both donor and receptor compartments were thermostatically controlled at a constant temperature by circulating 37° C. water through the water jacket compartment by means of an external circulator. The skin sample (human cadaver skin) used in the investigations was then mounted between the two half-cells. In the donor compartment was placed the formulation containing the pharmacologically active agent (i.e., the agent and permeation enhancement composition) and in the receptor compartment was placed Sorensen's phosphate buffer (pH 7.4), 0.9% saline solution or 40% propylene glycol/water solution. During the diffusion period (usually from about 0 to about 48 hours) samples were withdrawn periodically from the receptor compartment and subjected to HPLC analysis for a determination of the concentration of the pharmacologically active agent therein.

EXAMPLE 1

Table I depicts the results of a permeation study which was conducted through human cadaver skin as described above for the free base of a dihydropyridine calcium channel antagonist formulated, as by thorough mixing, with various permeation enhancement compositions of the present invention. This dihydropyridine (referred to in Table I as "test compound") is a potent coronary and peripheral vasodilator and is chemically (+)-1,4-dihydro-2,6-dimethyl-4-(3-nitrophenyl)-3,5-pyridinedicarboxylic acid, methyl 1-(phenylmethyl)-3-pyrrolidinyl ester. In Table I (and subsequent tables) all amounts shown are in parts by weight unless specifically denoted otherwise therein.

TABLE I

| Composition | Compound[a] | Ethanol | Azone | Water | PG[b] | Flux[c] |
|---|---|---|---|---|---|---|
| A | 1.0 | 52 | 3 | 45 | — | 2.12 |
| B | 1.0 | 62 | 3 | 35 | — | 0.65 |
| C | 1.0 | 82 | 3 | 15 | — | 0.25 |
| D | 2.5 | 95 | 5 | — | — | 0.22 |
| E | 2.5 | 100 | — | — | — | 0.12 |
| F | 20.0 | — | 100 | — | — | 0.04 |
| G | 1.0 | 40 | 3 | 40 | 20 | 14.76 |
| H | 1.0 | 40 | 2 | 40 | 20 | 8.90 |
| I | 0.5 | 37 | 3 | 40 | 20 | 8.44 |
| J | 1.0 | 40 | 1 | 40 | 20 | 1.90 |
| K | 1.0 | 40 | 0.5 | 40 | 20 | 1.29 |
| L | 1.0 | 52 | 3 | 25 | 20 | 0.51 |
| M | 1.0 | — | 10 | 3 | 87 | 0.21 |
| N | 0.5 | — | 5 | 63 | 32 | 0.01 |

[a] The amount of the test compound present in the donor compartment of the skin permeation cell at the start of the investigation
[b] Propylene glycol
[c] Refers to the steady state flux (rate of permeation) of the test compound through the skin sample in micrograms per square centimeter per hour (mcg/cm$^2$/hour)

Compositions A and B show enhanced flux over compositions C-F. Compositions A and B have all the components within their recommended range. Composition A has all the components within their preferred range. Compositions C and D demonstrate the effect of having the ethanol concentration increased beyond the recommended range. Composition D demonstrates the effect of having the ethanol concentration increased beyond the recommended range while the azone concentration is within its recommended range. Compositions E and F demonstrate the effect of increasing the ethanol and azone concentration, respectively, outside their recommended range.

Compositions G-K show enhanced flux over compositions L, M, and N. Compositions G-K have all the components within their recommended range. Compositions G and H and J and K demonstrate the effect of decreasing azone while keeping all components within their recommended range. Composition L demonstrates the effect of increasing the ethanol concentration while keeping the other components within their recommended range. Composition M demonstrates the effect of having decreased ethanol concentration, and increased azone and propylene glycol concentration. Composition N demonstrates the effect of decreased ethanol while the other components are within their recommended range.

EXAMPLE 2

A second pharmacologically active agent was assessed using human cadaver skin in the skin permeation cell according to the methods described above. This test compound possesses both positive inotropic and vasodilator activities and is chemically 1,3-dihydro-3, 3-dimethyl-5-(1,4,5,6-tetrahydro-6-oxo-3-pyridazinyl)-2H-indol-2-one. The results of this study are shown in Table II.

TABLE II

| Composition | Compound[a] | Ethanol | Azone | Water | PG[b] | Flux[c] |
|---|---|---|---|---|---|---|
| A | 0.3[d] | 52 | 3 | 45 | — | 6.75 |
| B | 0.3[d] | 97 | 3 | — | — | 0.36 |
| C | 0.3[d] | 37 | 3 | 40 | 20 | 13.80 |
| D | 0.3[d] | — | 5 | — | 95 | 0.21 |

[a], [b], [c] As defined in Table I
[d] Formulated with 2 parts by weight hydroxypropyl cellulose as a gelling agent Composition A shows enchanced flux over composition B. In composition A. all the components were kept within their recommended range. Composition B demonstrates the effect of having the ethanol concentration above the recommended range.

Composition C shows enhanced flux over composition D. In composition C, all components were kept within their recommended range. Composition D demonstrates the effects of having the ethanol concentration below the recommended range and propylene glycol concentration above the recommended range.

EXAMPLE 3

Table III shows the results of a permeation study through human cadaver skin using the methods described above for a test compound known as pinacidil, (±)-N-cyano-N'-4-pyridinyl-N''-(1,2,2-trimethylpropyl)guanidine, monohydrate. Pinacidil is pharmacologically active as an antihypertensive agent.

TABLE III

| Composition | Compound[a] | Ethanol | Azone | Water | PG[b] | Flux[c] |
|---|---|---|---|---|---|---|
| A | 2.0[d] | 52 | 3 | 45 | — | 31.78 |
| B | 5.0[d] | 97 | 3 | — | — | 0.59 |
| C | 5.0[d] | 100 | — | — | — | 0.70 |
| D | 2.0[d] | 37 | 3 | 40 | 20 | 33.83 |
| E | 5.0[d] | 70 | — | 10 | 20 | 0.35 |

[a], [b], [c] As defined in Table I
[d] Formulated with 2 parts by weight hydroxypropyl cellulose as a gelling agent Composition A shows enhanced flux over compositions B and C. Composition A has all components within their recommended range. Composition B demonstrates the effect of having the ethanol concentration increased beyond the recommended range while the azone concentration is within its recommended range. Compositions B and C demonstrate the effect of having increased ethanol concentration above the recommended range.

Composition D shows enhanced flux over composition E. Composition D has all components within their recommended range. Composition E demonstrates the effect of having the ethanol concentration increased and the azone concentration decreased beyond their recommended range.

EXAMPLE 4

A fourth pharmacologically active agent was assessed using human cadaver skin in the skin permeation cell according to the methods described above. This test compound is the free base of a dopamine agonist and is chemically trans(−)5,5A,6,7,8,9,9A,10-octahydro-6-propylpyrimidino(4,5-G)quinolin-2-amine. The results of this study are shown in Table IV.

TABLE IV

| Composition | Compound[a] | Ethanol | Azone | Water | PG[b] | Flux[c] |
|---|---|---|---|---|---|---|
| A | 1.0 | 52 | 3 | 45 | — | 15.65 |
| B | 0.6 | 50 | — | 50 | — | 4.00 |
| C | 1.0 | 34.4 | 0.6 | 45 | 20 | 21.70 |
| D | 1.0 | 34.4 | 3.4 | 42.2 | 20 | 29.40 |
| E | 1.0 | 30 | 2 | 48 | 20 | 32.20 |
| F | 1.0 | 37 | 3 | 40 | 20 | 16.10 |
| G | 1.0 | 45 | 4 | 31 | 20 | 14.60 |
| H | 1.0 | 45 | 5 | 40 | 10 | 11.20 |
| I | 1.0 | 60 | 2 | 18 | 20 | 1.80 |
| J | 1.0 | 45 | — | 35 | 20 | 3.20 |
| K | 0.6 | 40 | — | 40 | 20 | 3.30 |
| L | 0.6 | — | — | 60 | 40 | 0.30 |
| M | 0.6 | — | — | — | 100 | 0.00 |

[a, b, c]As defined in Table I

Composition A shows enhanced flux over composition B. Composition A has all the components within their recommended range. Composition B demonstrates the effect of having the azone concentration below the recommended range.

Compositions C–H show enhanced flux over compositions I–M. Compositions C and D demonstrate the effect of increasing the azone concentration while keeping all the components within the recommended range. Compositions E–H demonstrate the effect of increasing the ethanol concentration and the azone concentration while keeping all the components within their recommended range. Composition I demonstrates the effect of increasing the ethanol concentration beyond the preferred recommended range. Compositions J and K demonstrate the effect of decreasing the azone concentration below the recommended range. Composition L demonstrates the effect of decreasing the ethanol and the azone concentration below their recommended range. Composition M demonstrates the effect of increasing the propylene glycol concentration above its recommended range while decreasing the ethanol and azone concentration below their recommended range.

I claim:

1. A permeation enhancement composition for providing increased percutaneous absorption of an effective amount of an agent selected from (+)-1,4-dihydro-2,6-dimethyl-4-(3-nitrophenyl-3,5-pyridinedicarboxylic acid, methyl 1-(phenyimethyl)-3-pyrrolidinyl ester; 1,3-dihydro-3,3-dimethyl-5-(1,4,5,6-tetrahydro-6-oxo-3-pyridazinyl)2H-indol-2-one; (±)-N-cyano-N'-4-pyridinyl-N''-(1,2,2-trimethylpropyl) guanidine, monohydrate; and trans(−)5,5A,6,7,8,9,9A,10-octahydro-6-propylpyrimidino (4,5-G)-quinoline-2-amine; and further comprising from 30 to 70 parts by weight ethanol, from 0.1 to 10 parts by weight azone and from 30 to 69.9 parts by weight water; providing that emulsifiers and gelling agents are absent.

2. The composition of claim 1 containing from 35 to 69.9 parts by weight ethanol, from 0.1 to 10 parts by weight azone and from 35 to 80 parts by weight water.

3. The composition of claim 2 containing 52 parts by weight ethanol, 3 parts by weight azone and 45 parts by weight water.

4. The composition of claim 3 present in a pharmaceutical dosage form and additionally containing and effective amount of a pharmacologically active agent and pharmaceutically-acceptable excipients.

5. In a method for the percutaneous administration of an effective amount of an agent selected from (±)-1,4-dihydro-2,6-dimethyl-4-(3-nitrophenyl)-3,5 -pyridinedicarboxylic acid, methyl 1-(phenylmethyl)-3-pyrrolidinyl ester; 1,3-dihydro-3,3-dimethyl-5-(1,4,5,6-tetrahydro-6-oxo-3-pyridazinyl)2H-indol-2-one; (±)-N-cyano-N'-4-pyridinyl-N''-(1,2,2-trimethylpropyl)guanidine, monohydrate; and trans(−)5,5A,6,7,8,9,9A,10-octahydro-6-propylpyrimidino(4,5-G)quinoline-2-amine which includes placing and maintaining on a body surface a source of said agent and a permeation enhancement composition therefor in agent and composition transmitting relationship on said body surface, the improvement wherein said permeation enhancement composition is a composition of claim 1.

6. The method of claim 5 wherein said permeation enhancement composition contains from 35 to 69.9 parts by weight ethanol, from 0.1 to 10 parts by weight azone and from 35 to 80 parts by weight water.

7. The method of claim 6 wherein said permeation enhancement composition contains 52 parts by weight ethanol 3 parts by weight azone and 45 parts by weight water.

8. The method of claim 7 wherein the pharmacologically active agent and the permeation enhancement composition are present in a pharmaceutical dosage form additionally containing pharmaceutically-acceptable excipients.

* * * * *

UNITED STATES PATENT AND TRADEMARK OFFICE
CERTIFICATE OF CORRECTION

PATENT NO. : 5,196,416
DATED : March 23, 1993
INVENTOR(S) : Kirti H. Valia

It is certified that error appears in the above-indentified patent and that said Letters Patent is hereby corrected as shown below:

Claim 1, column 7, line 45, delete "1-(phenyimethyl)" and insert therefor —1-(phenylmethyl)—.

Claim 4, column 8, line 15, delete the word "and" at the end of the line and insert —an—.

Claim 6, column 8, line 37, delete "80 parts" and insert therefor —69.9 parts—.

Column 8, line 35, "69.9" should be —70—.

Signed and Sealed this

Fifteenth Day of February, 1994

Attest:

BRUCE LEHMAN

*Attesting Officer*    Commissioner of Patents and Trademarks